United States Patent
Yanai et al.

(10) Patent No.: US 7,033,147 B2
(45) Date of Patent: Apr. 25, 2006

(54) CENTRIFUGAL FLUID PUMP ASSEMBLY WITH FLOW RATE CALCULATING SECTION

(75) Inventors: Masamichi Yanai, Nakai-machi (JP); Mitsutoshi Yaegashi, Nakai-machi (JP)

(73) Assignee: Terumo Kabushiki Kaisha, Tokyo (JP)

( * ) Notice: Subject to any disclaimer, the term of this patent is extended or adjusted under 35 U.S.C. 154(b) by 122 days.

(21) Appl. No.: 10/352,098

(22) Filed: Jan. 28, 2003

(65) Prior Publication Data
US 2003/0223879 A1 Dec. 4, 2003

(30) Foreign Application Priority Data
Jan. 28, 2002 (JP) ........................................ 2002-018570

(51) Int. Cl.
*F04B 17/00* (2006.01)

(52) U.S. Cl. ................................ 417/410.1; 417/44.11; 417/293; 417/22; 417/24; 417/32
(58) Field of Classification Search .............. 417/410.1, 417/293, 22, 24, 32, 43, 44.1, 44.11
See application file for complete search history.

(56) References Cited

U.S. PATENT DOCUMENTS

| 5,578,752 | A | * | 11/1996 | Schlecht et al. ............... 73/239 |
| 5,615,996 | A | * | 4/1997 | Suzuki et al. ................... 415/1 |
| 5,619,433 | A | * | 4/1997 | Wang et al. ................... 703/18 |
| 5,704,767 | A | * | 1/1998 | Johnson ........................ 417/43 |
| 5,725,357 | A | * | 3/1998 | Nakazeki et al. .............. 417/18 |
| 6,129,660 | A | | 10/2000 | Nakazeki et al. |
| 6,142,752 | A | | 11/2000 | Akamatsu et al. |
| 6,388,346 | B1 | * | 5/2002 | Lopatinsky et al. ........... 310/63 |
| 6,866,625 | B1 | * | 3/2005 | Ayre et al. ..................... 600/16 |
| 2003/0033859 | A1 | | 2/2003 | Schoeb et al. |
| 2003/0035730 | A1 | | 2/2003 | Schob |
| 2004/0152944 | A1 | * | 8/2004 | Medvedev et al. ........... 600/17 |

FOREIGN PATENT DOCUMENTS

| EP | 1 284 369 A1 | 2/2003 |
| WO | WO 01/72352 A2 | 10/2001 |

* cited by examiner

Primary Examiner—Charles G. Freay
Assistant Examiner—Emmanuel Sayoc
(74) Attorney, Agent, or Firm—Buchanan Ingersoll PC

(57) ABSTRACT

A centrifugal fluid pump assembly includes a body section and a control mechanism 6. The body section includes a housing, an impeller rotatable within the housing, and a motor for rotating the impeller. The pump assembly includes a motor current flow rate-related data storage section for storing, for a plurality of different predetermined viscosities, predetermined viscosity-related flow rate data formed from a plurality of motor current flow rate relation data at a plurality of different impeller rotational speeds at predetermined fluid viscosity, a fluid measurement data inputting section, an impeller rotational speed measurement function, a motor current measurement function, and a flow rate calculating section 58 for using a fluid viscosity value, an impeller rotational speed value, a measured motor current and data stored in the motor current flow rate-related data storage section to calculate a fluid flow rate.

14 Claims, 11 Drawing Sheets

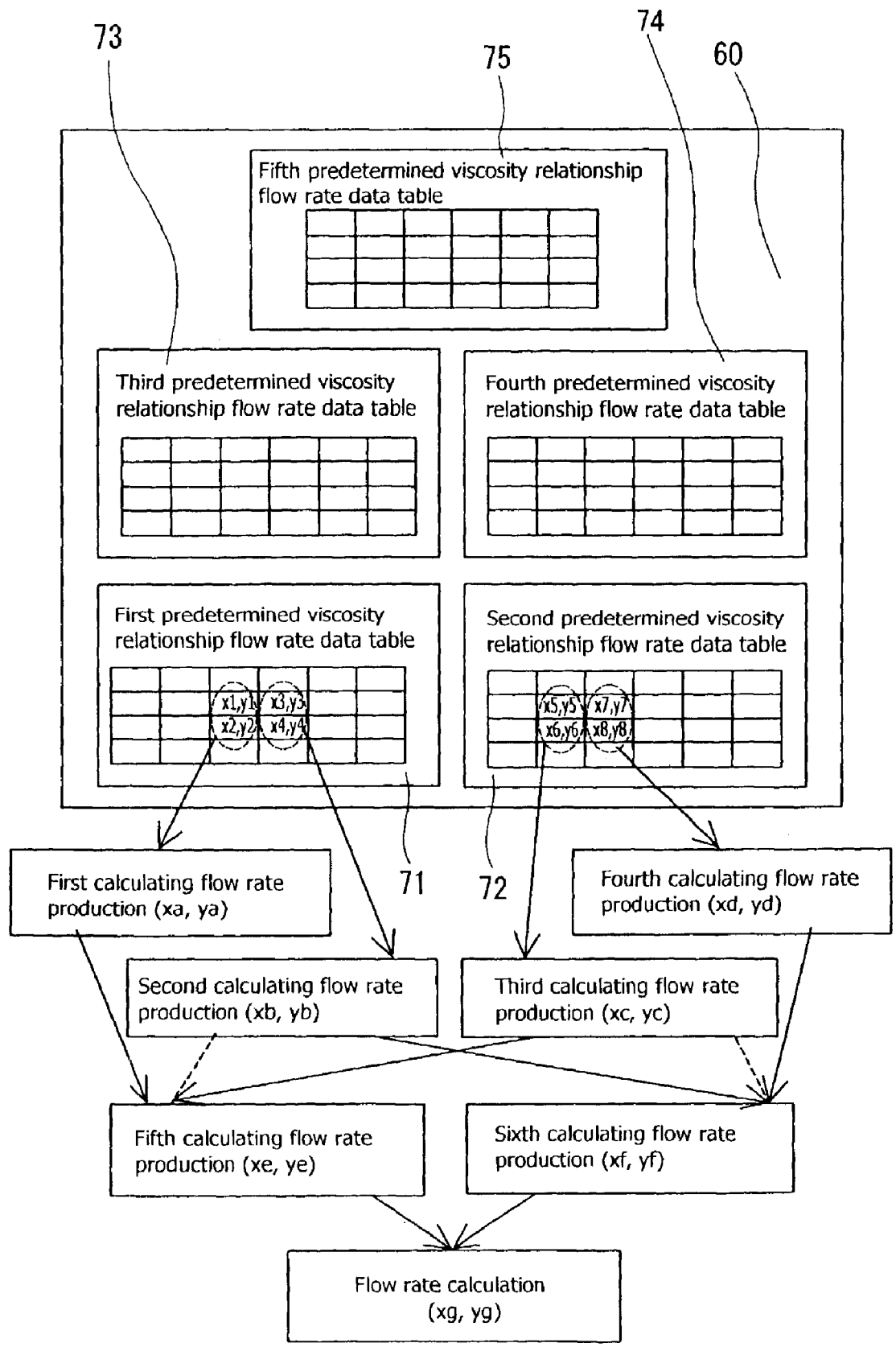

FIG.8

Flow rate data table for viscosity of 1cP

| Flow rate | Motor rotational speed | | | | |
|---|---|---|---|---|---|
| | ...rpm | 1600rpm | 1800rpm | 2000rpm | 2200rpm |
| ..L/min | .... | .... | .... | .... | .... |
| 2L/min | .... | 0.13A | 0.16A | 0.20A | .... |
| 3L/min | .... | 0.15A | 0.19A | 0.23A | .... |
| 4L/min | .... | 0.17A | 0.22A | 0.27A | .... |
| 5L/min | .... | 0.19A | 0.24A | 0.30A | .... |
| 6L/min | .... | 0.22A | 0.28A | 0.34A | .... |
| ... | .... | .... | .... | .... | .... |

FIG.9

Flow rate data table for viscosity of 2cP

| Flow rate | Motor rotational speed | | | | |
|---|---|---|---|---|---|
| | ......rpm | 1600rpm | 1800rpm | 2000rpm | 2200rpm |
| ..L/min | .... | .... | .... | .... | .... |
| 2L/min | .... | 0.14A | 0.18A | 0.22A | .... |
| 3L/min | .... | 0.16A | 0.20A | 0.25A | .... |
| 4L/min | .... | 0.18A | 0.23A | 0.28A | .... |
| 5L/min | .... | 0.20A | 0.25A | 0.31A | .... |
| 6L/min | .... | 0.23A | 0.29A | 0.36A | .... |
| ... | .... | .... | .... | .... | .... |

FIG.10

Flow rate data table for viscosity of 3cP

| Flow rate | Motor rotational speed | | | | |
|---|---|---|---|---|---|
| | ......rpm | 1600rpm | 1800rpm | 2000rpm | 2200rpm |
| ..L/min | .... | .... | .... | .... | .... |
| 2L/min | .... | 0.15A | 0.19A | 0.24A | .... |
| 3L/min | .... | 0.17A | 0.22A | 0.27A | .... |
| 4L/min | .... | 0.19A | 0.25A | 0.30A | .... |
| 5L/min | .... | 0.22A | 0.27A | 0.34A | .... |
| 6L/min | .... | 0.25A | 0.31A | 0.39A | .... |
| ... | .... | .... | .... | .... | .... |

FIG.11

Flow rate data table for viscosity of 4cP

| Flow rate | Motor rotational speed | | | | |
|---|---|---|---|---|---|
| | ......rpm | 1600rpm | 1800rpm | 2000rpm | 2200rpm |
| ..L/min | .... | .... | .... | .... | .... |
| 2L/min | .... | 0.16A | 0.21A | 0.26A | .... |
| 3L/min | .... | 0.19A | 0.24A | 0.29A | .... |
| 4L/min | .... | 0.21A | 0.27A | 0.33A | .... |
| 5L/min | .... | 0.23A | 0.30A | 0.36A | .... |
| 6L/min | .... | 0.27A | 0.34A | 0.42A | .... |
| ... | .... | .... | .... | .... | .... |

FIG.12

Flow rate data table for viscosity of 5cP

| Flow rate | Motor rotational speed | | | | |
|---|---|---|---|---|---|
| | ......rpm | 1600rpm | 1800rpm | 2000rpm | 2200rpm |
| ..L/min | .... | .... | .... | .... | .... |
| 2L/min | .... | 0.18A | 0.22A | 0.28A | .... |
| 3L/min | .... | 0.20A | 0.26A | 0.31A | .... |
| 4L/min | .... | 0.23A | 0.29A | 0.35A | .... |
| 5L/min | .... | 0.25A | 0.32A | 0.39A | .... |
| 6L/min | .... | 0.29A | 0.37A | 0.45A | .... |
| ... | .... | .... | .... | .... | .... |

CENTRIFUGAL FLUID PUMP ASSEMBLY WITH FLOW RATE CALCULATING SECTION

BACKGROUND OF THE INVENTION

This invention relates to a centrifugal fluid pump assembly for pumping a medical fluid such as blood.

A centrifugal blood pump is one type of pump used in artificial heart units. A centrifugal blood pump includes a housing having a blood inlet and a blood outlet, and an impeller which rotates within the housing for feeding blood by centrifugal force upon rotation thereof. One of the significant parameters for grasping that the blood pump functions correctly on a living organism is the flow rate. The flow rate may be measured directly using a sensor for exclusive use such as an ultrasonic flow meter. However, the direct measurement of the flow rate is inferior in terms of stable continuous monitoring for a long period of time. Further, an increase of the number of parts leads to increase the size of the apparatus. Therefore, a system is expected wherein the flow rate is measured indirectly from the motor speed (rotation speed) of the pump, electric current flowing through the motor (motor current), the viscosity and the specific gravity of blood and/or like parameters without the provision of a flow meter.

In an indirect measurement system, the flow rate can be calculated by correcting a value calculated regarding the flow rate as a function of the motor speed and the motor current with a viscosity factor. In particular, the flow rate is calculated from the speed of rotation and the motor current of the motor which can be measured directly. In this instance, it is possible to determine a correlation between the motor speed, the motor current and the flow rate in advance and use an approximate expression calculated from the correlation. The approximate expression can be represented, for example, as the following expression (1):

$$i = \sum_{k=0}^{2} \sum_{l=0}^{2} \sum_{m=0}^{2} c_{k/m} v^k n^l q^m \quad (1)$$

where $c_{klm}$ is a coefficient calculated by the method of least squires, i [A] is the motor current, v [mPa·s(cP)] is the viscosity, n [rpm] is the speed of rotation, and q [L/min] is the flow rate.

Where such a polynomial as given above is used, however, if the degree of approximation is lowered, then the accuracy basically in the overall region drops including data points (sample points used in the terminology of interpolation). On the other hand, if the degree of approximation is raised, then unnecessary oscillation which is a drawback in polynomial interpolation takes place, and also this gives rise to a drop the accuracy except data points.

In order to prevent such a drop of the accuracy as described above, it is possible to prepare and refer to a large amount of data in a table to use a flow rate in the conditions nearest to a given motor speed and a given motor current as an estimated value. However, according to this system, an increased area for storing data is required, and an increase of processing of searching the storage area increases a load upon a controller for the pump. Thus, if the controller is a portable type, it is difficult to display the flow rate on the real time basis on the controller.

Also where spline interpolation is used as the interpolation, there is a problem that a great amount of calculation is required although the problem of the accuracy is solved.

It is an object of the present invention to provide a centrifugal fluid pump assembly which has a flow rate calculation function by which the fluid flow rate (discharge) can be calculated readily and with certainty without using a flow meter.

It is another object of the present invention to provide a magnetically levitated centrifugal pump wherein minimum discrete data with which a necessary accuracy can be satisfied are stored without having a relational expression between the motor speed, motor current, viscosity and flow rate, and their stored data which are proximate to an motor current value and so forth of an object of calculation are used to calculate the flow rate.

SUMMARY OF THE INVENTION

In accordance with the present invention, the objects described above are achieved by a centrifugal fluid pump assembly which includes a housing having a fluid inlet and a fluid outlet, an impeller rotatable within the housing for feeding fluid by centrifugal force upon rotation thereof, and a motor for rotating the impeller, including a motor current flow rate-related data storage section for storing, for a plurality of different predetermined viscosities, predetermined viscosity-related flow rate data formed from a plurality of motor current flow rate relation data at a plurality of different impeller rotational speeds at predetermined fluid viscosity, a fluid measurement data inputting section, an impeller rotational speed measurement function or an impeller rotational speed calculation function, a motor current measurement function, and a flow rate calculating section for calculation, using a fluid viscosity value inputted to the fluid measurement data inputting section or calculated from fluid measurement data inputted to the fluid measurement data inputting section, an impeller rotational speed value obtained by the impeller rotational speed measurement function or impeller rotational speed calculation function, a measured motor current obtained by the motor current measurement function and the data stored in the motor current flow rate-related data storage section, a fluid flow rate at the fluid viscosity value, the measured motor current and the impeller rotational speed value.

BRIEF DESCRIPTION OF THE DRAWINGS

FIG. 7 is a diagrammatic view illustrating a data structure and a flow rate calculating procedure of a motor current flow rate-related data storage section;

FIGS. 8 to 12 are diagrammatic views illustrating different particular examples of a predetermined viscosity-related data table stored in the motor current flow rate-related data storage section;

DETAILED DESCRIPTION OF THE PREFERRED EMBODIMENTS

Figure 1:
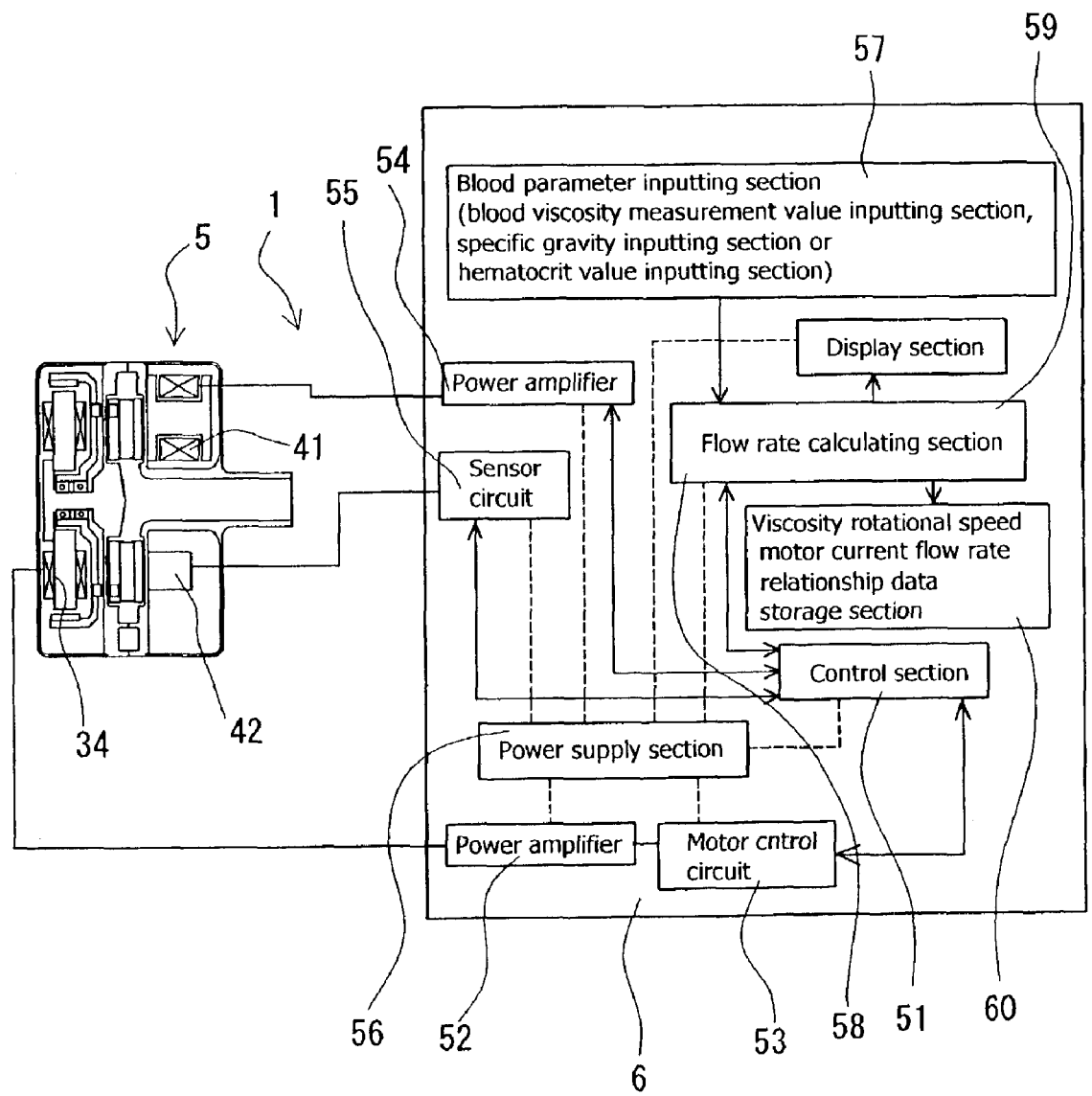
FIG. 1 is a block diagram of an embodiment of a centrifugal pump assembly of the present invention.
Figure 2:
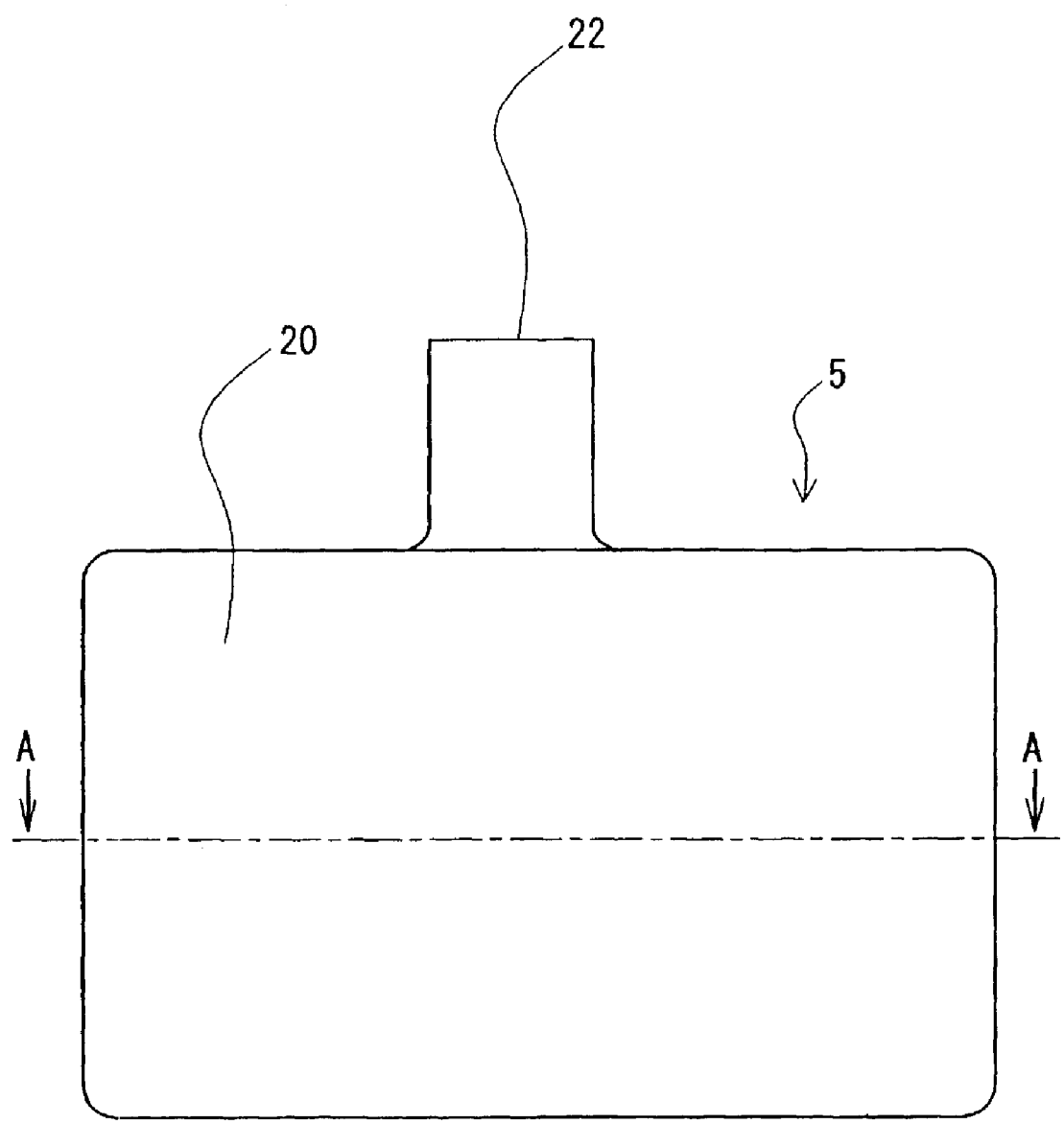
FIG. 2 is a front elevational view of an example of a centrifugal pump assembly body section used in the centrifugal pump apparatus of the present invention.

A centrifugal fluid pump assembly of the present invention is described in connection with preferred embodiments wherein it is applied to a blood pump.

The centrifugal fluid pump assembly 1 of the present invention includes a housing 20 having a fluid inlet 22 and a fluid outlet 23, an impeller 21 rotatable within the housing 20 for feeding fluid by centrifugal force upon rotation thereof, and a motor 34 for rotating the impeller 21.

The centrifugal fluid pump assembly 1 further includes a motor current flow rate-related data storage section (in other words, viscosity rotational speed motor current flow rate-related data storage section, also in other words, relational data between flow rate and motor current storage section) 60 for storing, for a plurality of different predetermined fluid viscosities (in other words, some different fixed viscosities), predetermined (or fixed) viscosity-related flow rate data formed from a plurality of motor current flow rate-related data (in other words, relational data between flow rate and motor current) at a plurality of different impeller rotational speeds (in other words, some different fixed impeller rotational speeds) at predetermined (or fixed) fluid viscosity, a fluid measurement data inputting section (in other words, fluid viscosity-related measurement data inputting section) 57, an impeller rotational speed measurement function or an impeller rotational speed calculation function, a motor current measurement function, and a flow rate calculating section 58 for using a fluid viscosity value inputted to the fluid measurement data inputting function or calculated from a fluid measurement data inputted to the fluid measurement data inputting function, an impeller rotational speed value obtained by the impeller rotational speed measurement function or impeller rotational speed calculation function, a measured motor current obtained by the motor current measurement function and the data stored in the motor current flow rate-related data storage section 60 to calculate the fluid flow rate at the fluid viscosity value, the measured motor current and the impeller rotational speed value.

Since the flow rate is calculated using the data stored in the motor current flow rate-related data storage section 60 which stores, for a plurality of different predetermined viscosities (some different fixed viscosities), predetermined viscosity-related flow rate data formed from a plurality of motor current flow rate-related data at a plurality of different impeller rotational speeds at predetermined fluid viscosity in this manner, the fluid flow rate (discharge) can be calculated readily and with certainty without using a flow meter. Further, the fluid flow rate (discharge) can be calculated more quickly than where a high degree calculating expression is used for the calculation.

Further, the fluid pump assembly of the embodiment shown in FIGS. 1 to 5 includes a centrifugal fluid pump section 2a including housing 20 having a fluid inlet 22 and a fluid outlet 23 and an impeller 21 having magnetic members 25 provided in the inside thereof and rotatable within the housing 20 for feeding fluid by centrifugal force upon rotation thereof, an impeller rotating torque generation section 3 including a rotor 31 including magnets 33 for attracting the magnetic members 25 of the impeller 21 of the centrifugal fluid pump section 2 and a motor 34 for rotating the rotor 31, and a impeller position control section 4 including an electromagnet 41. In the fluid pump assembly, the impeller 21 rotates in a non-contacting relationship with the housing 20.

It is to be noted that the centrifugal blood pump assembly of the present invention can be applied not only to such an apparatus of the type wherein the impeller rotates in a non-contacting relationship as described above, but also to an apparatus of the type wherein, for example, the impeller is connected to a shaft of a motor so that it is rotated by rotation of the motor.

As shown in FIGS. 2 to 6, a centrifugal fluid pump assembly body section 5 in the present embodiment includes a housing 20 having a fluid inlet 22 and a fluid outlet 23, a centrifugal fluid pump section 2 having an impeller 21 rotatable within the housing 20 for feeding blood by centrifugal force upon rotation thereof, an impeller rotating torque generation section (uncontrolled magnetic bearing section) 3 for the impeller 21, and an impeller position control section (controlled magnetic bearing section) 4 for the impeller 21.

Figure 4:
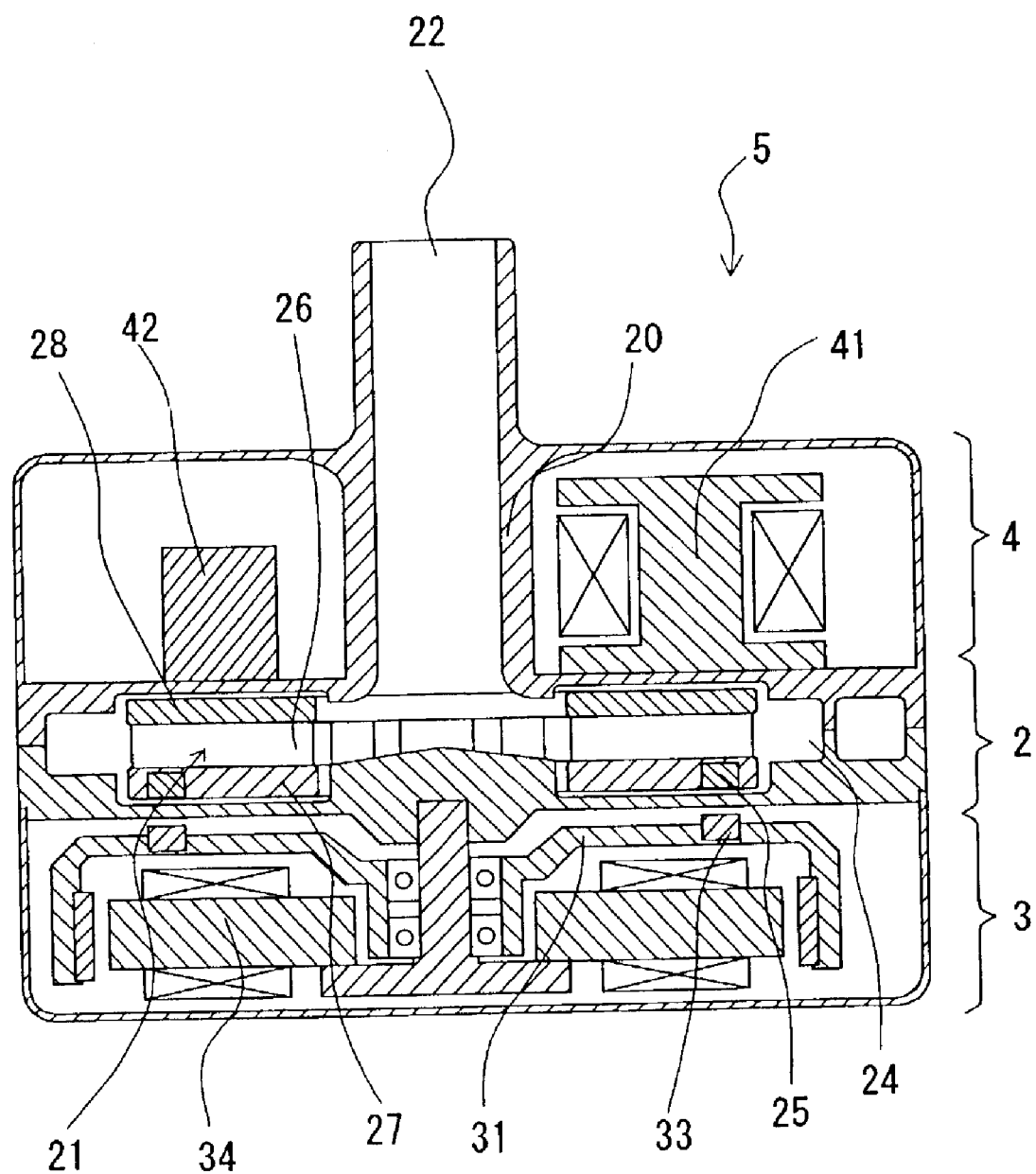
FIG. 4 is a vertical sectional view of the centrifugal pump assembly body section of the embodiment shown in FIG. 2.

Referring to FIG. 4, the impeller 21 is held at a predetermined position in the housing 20 and normally rotates without contacting with an inner face of the housing 20 by an action of the uncontrolled magnetic bearing section 3 and the controlled magnetic bearing section 4.

Figure 3:
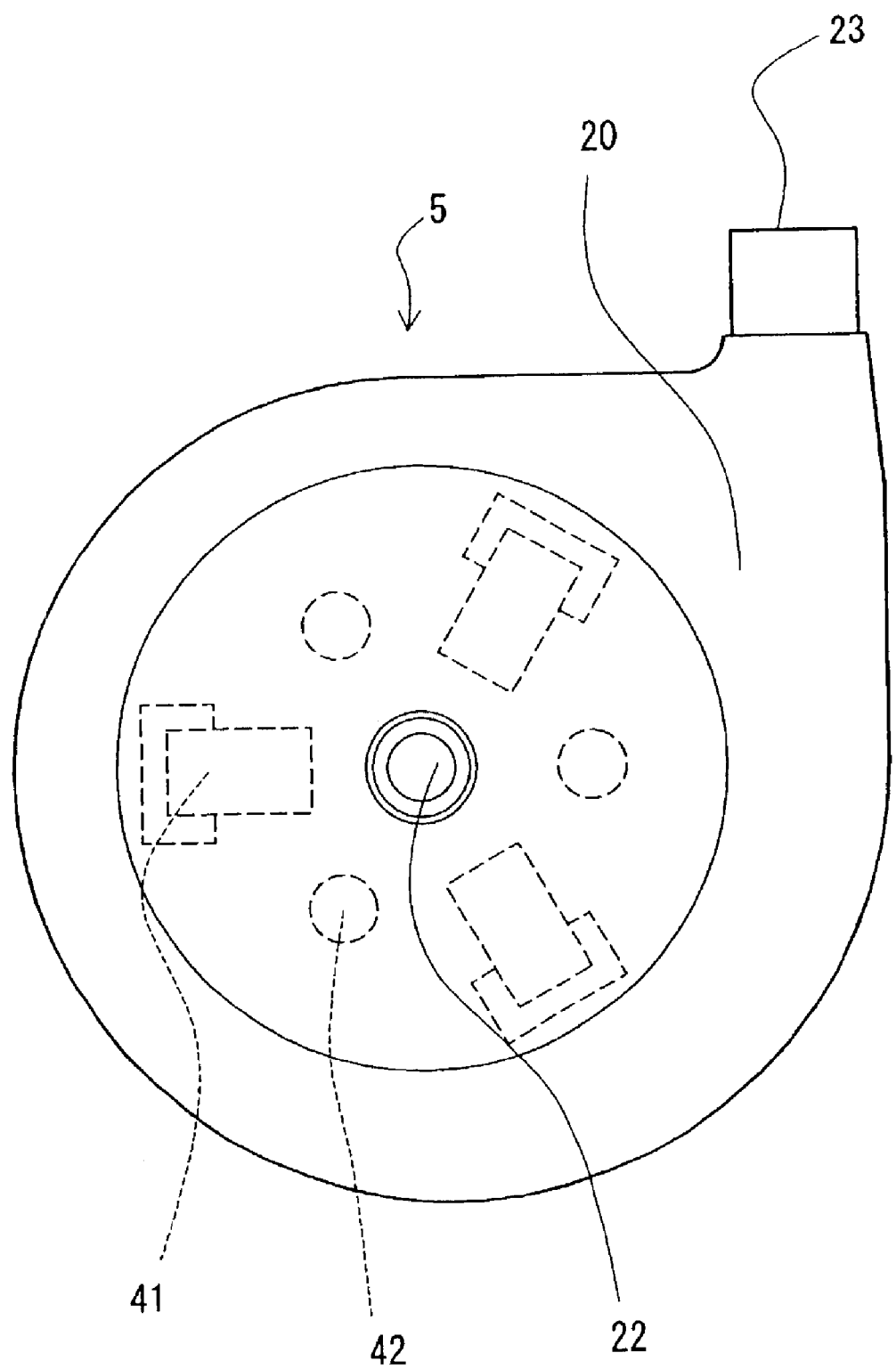
FIG. 3 is a plan view of the centrifugal pump assembly body section shown in FIG. 2.

The housing 20 has a fluid inlet 22 and a fluid outlet 23 and is formed from a nonmagnetic material. The housing 20 has a blood chamber 24 formed therein for communication with the fluid inlet 22 and the fluid outlet 23. The impeller 21 is accommodated in the housing 20. The fluid inlet 22 is provided such that it projects substantially vertically from a central portion of an upper face of the housing 20. The fluid outlet 23 is provided such that it projects in a tangential direction from a side face of the housing 20 formed in a substantially cylindrical shape as shown in FIGS. 3 and 5.

Figure 5:
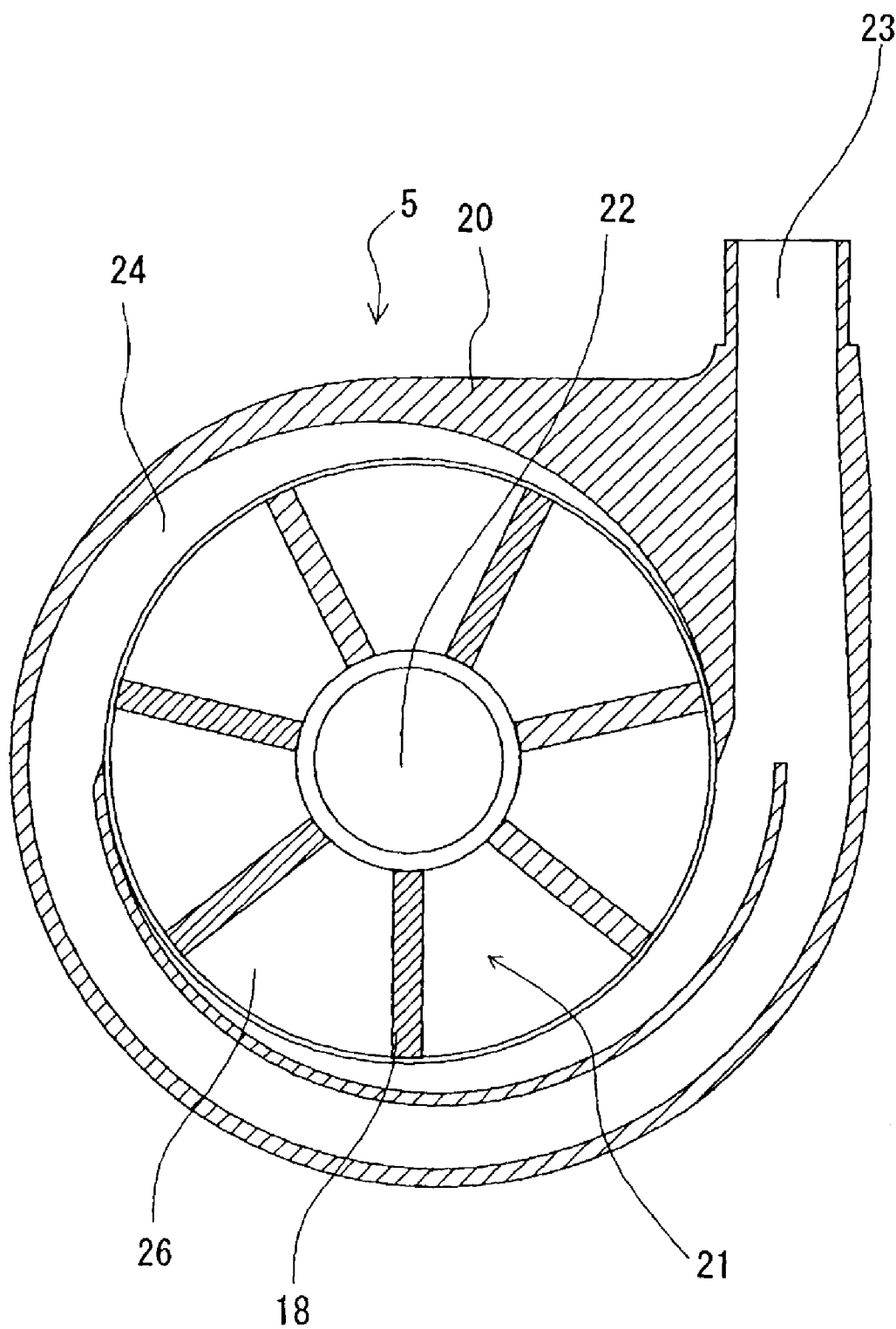
FIG. 5 is a sectional view taken along line A—A of FIG. 2.

Referring to FIG. 5, the impeller 21 in the form of a disk having a through-hole formed at the center thereof is accommodated in the blood chamber 24 formed in the housing 20. Referring to FIG. 4, the impeller 21 has a doughnut-shaped plate member (lower shroud) 27 which forms the bottom wall, another doughnut-shaped plate member (upper shroud) 28 which forms the top wall and is open at the center thereof, and a plurality of (for example, seven) vanes 18 formed between the doughnut-shaped plate member 27 and the doughnut-shaped plate member 28. A plurality of (seven) blood passages 26 partitioned by adjacent ones of the vanes 18 are formed between the lower shroud 27 and the upper shroud 28. The blood passages 26 are communicated with the central opening of the impeller 21 as shown in FIG. 5 and extend from the central opening of the impeller 21 such that the width thereof increases gradually to the outer circumferential edge of the impeller 21. In other words, the vanes 18 are formed between adjacent ones of the blood passages 26. It is to be noted that, in the present embodiment, the blood passages 26 and the vanes 18 are provided at equal angle and in substantially same shapes.

Referring to FIG. 4, the impeller 21 has a plurality of (for example, 24) first magnetic members 25 (permanent magnets, driven magnets) embedded therein. In the present embodiment, the first magnetic members 25 are embedded in the lower shroud 27. The embedded magnetic members 25 (permanent magnets) are provided so as to be attracted by the permanent magnets 33 provided on the rotor 31 of the impeller rotating torque generation section 3, which is hereinafter described, to urge the impeller 21 away from the inlet 22 thereby to transmit rotating torque from the impeller rotating torque generation section.

Further, where a suitable number of magnetic members 25 are embedded as in the present embodiment, also the magnetic coupling to the rotor 31 hereinafter described can be secured sufficiently. The magnetic members 25 (permanent magnets) preferably have a circular shape. Or, the magnetic members 25 may be formed by dividing a ring-shaped magnet into multiple poles (for example, 24 poles), or in other words, formed from a plurality of small magnets arranged in a ring-shape such that they have magnetic poles arranged alternately.

The impeller 21 further includes a second magnetic member 28 formed as the upper shroud itself or provided in the upper shroud. In the present embodiment, the entire upper shroud is formed from the magnetic member 28. The magnetic member 28 is provided to attract the impeller 21 toward the fluid inlet 22 by the electromagnet 41 of the impeller position control section hereinafter described. Magnetic stainless steel or a like material is used for the magnetic member 28.

A contactless magnetic bearing is formed from the impeller position control section 4 and the impeller rotating torque generation section 3, and the impeller 21 is attracted in the opposite directions by the impeller position control section 4 and the impeller rotating torque generation section 3 such that it rotates in a non-contacting relationship within the housing 20 stably at a suitable position at which it does not contact with the inner face of the housing 20.

Referring to FIG. 4, the impeller rotating torque generation section 3 includes a rotor 31 accommodated in the housing 20 and a motor 34 for rotating the rotor 31. The rotor 31 includes a plurality of permanent magnets 33 provided on a face thereof adjacent the centrifugal fluid pump section 2. The center of the rotor 31 is secured to a rotary shaft of the motor 34. The permanent magnets 33 are provided at equal angle so as to correspond to the arrangement form (quantity and arrangement positions) of the permanent magnets 25 of the impeller 21.

The impeller rotating torque generation section 3 need not necessarily include such a rotor and a motor as described above, but may otherwise include, for example, a plurality of stator coils for attracting the permanent magnets 25 of the impeller 21 and driving the impeller 21 to rotate.

Referring to FIGS. 3 and 4, the impeller position control section 4 includes a plurality of fixed electromagnets 41 for attracting the magnetic member 28 of the impeller 21, and a position sensor 42 for detecting the position of the magnetic member 28 of the impeller 21. More particularly, the impeller position control section 4 includes a plurality of electromagnets 41 accommodated in the housing 20, and a plurality of position sensors 42. The a plurality of (three) electromagnets 41 and the a plurality of (three) position sensors 42 of the impeller position control section 4 are individually provided at equal angle, and also the electromagnets 41 and the position sensors 42 are provided at equal angle. The electromagnets 41 are each formed from an iron core and a coil. The number of the electromagnets 41 in the present embodiment is three. The number of the electromagnet 41 may be three or more, for example, four. By providing three or more electromagnets 41 and adjusting the electromagnetic force of them using a detection result of the position sensors 42, the force components of the rotation axis (z-axis) of the impeller 21 can be balanced with each other and the moments around the x-axis and the y-axis perpendicular to the rotary shaft (z-axis) can be controlled.

The position sensors 42 detect the distance between the electromagnets 41 and the magnetic member 28, and detection outputs of the position sensors 42 are sent to a control section 51 of a control mechanism (in other words, controller) 6 for controlling the current or voltage to be applied to the coil of each of the electromagnets 41. Further, even if force in a radial direction originating from the force of gravity or the like acts upon the impeller 21, since shearing force of magnetic fluxes between the magnetic members 25 of the impeller 21 and the magnets 33 of the rotor 31 and shearing force between the electromagnets 41 and the magnetic member 28 act, the impeller 21 is kept at the center of the housing 20.

Referring to FIG. 1, the control mechanism 6 includes a power amplifier 52 and a motor control circuit 53 for the motor 34 for magnetic coupling, a power amplifier 54 for the electromagnets 41, a sensor circuit 55 for the position sensors 42, a sensor output monitoring section (not shown) for monitoring the sensor outputs, a control section 51, a power supply section 56, a fluid measurement data inputting section (in other words, blood parameter inputting section) 57, a flow rate calculating section 58, a display section 59, and a motor current flow rate-related data storage section (in other words, viscosity rotational speed motor current flow rate-related data storage section) 60. The control section 51 has a motor current monitoring function.

The fluid measurement data inputting section (blood parameter inputting section) 57 is, for example, a fluid viscosity measurement value inputting section. Preferably, the fluid measurement data inputting section (blood parameter inputting section) 57 includes a blood viscosity measurement value inputting section and a specific gravity inputting section as shown in FIG. 1. In this instance, the blood viscosity and the specific gravity are measured with blood gathered from a patient using an external instrument.

The fluid measurement data inputting section (blood parameter inputting section) 57 may be, for example, a hematocrit value inputting section as indicated in FIG. 1. In this instance, the centrifugal fluid pump assembly has a viscosity calculating function for calculation the viscosity from the inputted hematocrit value. In short, the flow rate calculating section 58 is provided with a viscosity calculating function. The viscosity calculating method is given by the following expression:

$$V = a_3 Hct^3 + a_2 Hct^2 + a_1 Hct + a_0$$

where V [mPa·s] is the viscosity, Hct [%] is the hematocrit value, and $a_0$ to $a_3$ are coefficients.

Further, the centrifugal fluid pump assembly preferably has a specific gravity calculating function for calculating the specific gravity from the inputted hematocrit value. In short, the flow rate calculating section 58 is provided with a specific gravity calculating function. The specific gravity calculation method is represented by the following expression:

$$\rho = b_3 Hct^3 + b_2 Hct^2 + b_1 Hct + b_0$$

where $\rho$ is the specific gravity, Hct [%] is the hematocrit value, and $b_0$ to $b_3$ are coefficients.

Preferably, the centrifugal fluid pump apparatus has a measured motor current correcting function for correcting a motor current actual measurement value with the inputted or calculated specific gravity to obtain a measured motor current. More particularly, the motor current actual measurement value is corrected in accordance with the following expression:

measured motor current=motor current actual measurement value/ specific gravity

Now, the flow rate calculating function of the flow rate calculating section is described.

The viscosity rotational speed motor current flow rate-related data storage section 60 of the control mechanism 6 stores, for a plurality of predetermined viscosities, predetermined viscosity-related flow rate data formed from a plurality of motor current flow rate-related data at a plurality of different impeller rotational speeds at predetermined fluid viscosity. More particularly, the viscosity rotational speed motor current flow rate-related data storage section 60 stores data for a plurality of different viscosities in the form of data tables each for a viscosity. In other words, the viscosity rotational speed motor current flow rate-related data storage section 60 stores a database regarding the viscosity, impeller rotational speed, motor current and flow rate. The data tables are different for the different viscosities and each of the viscosity tables stores a plurality of data regarding the rotational speed, motor current and flow rate, for example, as shown in FIGS. 8 to 12. More particularly, in the viscosity tables shown in FIGS. 8 to 12, motor current for a plurality of predetermined rotational speeds and a plurality of flow rates are recorded. It is to be noted that, although such data tables as described above are preferable for data recording, otherwise a plurality of data sets each including four parameters of the viscosity, motor rotational speed, motor current and flow rate may be stored.

More specifically, referring to FIG. 7, the motor current flow rate-related data storage section 60 includes at least a first predetermined viscosity-related flow rate data storage function (in other words, first predetermined viscosity-related flow rate data table) 71 for storing a plurality of data regarding the motor current and the flow rate at a plurality of impeller rotational speeds at a first predetermined fluid viscosity, a second predetermined viscosity-related flow rate data storage function (in other words, second predetermined viscosity-related flow rate data table) 72 for storing a plurality of data regarding the motor current and the flow rate at a plurality of impeller rotational speeds at a second predetermined fluid viscosity, and a third predetermined viscosity-related flow rate data storage function (in other words, third predetermined viscosity-related flow rate data table) 73 for storing a plurality of data regarding the motor current and the flow rate at a plurality of impeller rotational speeds at a third predetermined fluid viscosity. Particularly, the motor current flow rate-related data storage section 60 preferably includes a fourth predetermined viscosity-related flow rate data storage function (in other words, fourth predetermined viscosity-related flow rate data table) 74 for storing a plurality of data regarding the motor current and the flow rate at a plurality of impeller rotational speeds at a fourth predetermined fluid viscosity as in the present embodiment shown. Furthermore, the motor current flow rate-related data storage section 60 preferably includes a fifth predetermined viscosity-related flow rate data storage function (in other words, fifth predetermined viscosity-related flow rate data table) 75 for storing a plurality of data regarding the motor current and the flow rate at a plurality of impeller rotational speeds at a fifth predetermined fluid viscosity.

As seen in FIG. 7, the centrifugal fluid pump assembly 1 of the present embodiment includes first to fifth predetermined viscosity-related flow rate data tables 71 to 75. The pump assembly 1 may further include a sixth or further predetermined viscosity-related flow rate data tables. As the first to fifth predetermined viscosity-related flow rate data tables, the tables for different viscosity (mPa·s) different by an equal interval like 1, 2, 3, 4 and 5 are preferably provided, as shown in FIGS. 8 to 12. The data in the data tables were obtained in advance using fluid having a specific gravity of 1. Therefore, upon calculation of the flow rate, where the measured or calculated specific gravity is not equal to 1, a value obtained by dividing the measured current by the specific gravity is used.

The data stored in the predetermined viscosity-related flow rate data storage functions (predetermined viscosity-related data tables) preferably include a plurality of data regarding the motor current and the flow rate at a plurality of equal impeller rotational speeds.

The flow rate calculating section 58 uses the data stored in the viscosity rotational speed motor current flow rate-related data storage section 60, a viscosity value inputted to the fluid viscosity-related measurement data inputting section (blood parameter inputting section) 57 or a fluid viscosity value calculated from fluid measurement data (particularly, a hematocrit value) inputted to the fluid viscosity-related measurement data inputting section (blood parameter inputting section) 57, an impeller rotational speed value obtained by the impeller rotational speed measurement function or the impeller rotational speed calculation function and a measured motor current obtained by the motor current measurement function to calculate the fluid flow rate at the fluidity viscosity value, the measured motor current and the impeller rotational speed value.

More particularly, the flow rate calculating section 58 calculates the flow rate using the data of two predetermined viscosity-related flow rate data storage functions proximate to an inputted viscosity value or a fluid viscosity value calculated from inputted fluid measurement data (particularly, a hematocrit value). Further, if the inputted viscosity value or the fluid viscosity value calculated from inputted fluid measurement data (particularly, a hematocrit value) is equal to a predetermined viscosity of one of the predetermined viscosity-related flow rate data storage functions, then the flow rate calculating section 58 calculates the flow rate using the data of the predetermined viscosity-related flow rate data storage function. Furthermore, the flow rate calculating section 58 calculates the flow rate using those of the motor current flow rate relation data which relate to two impeller rotational speeds proximate to the impeller rotational speed value in data of two predetermined viscosity-related flow rate data storage functions proximate to an inputted viscosity value or a fluid viscosity value calculated from inputted fluid measurement data (particularly, a hematocrit value).

Further, in the centrifugal fluid pump assembly of the present embodiment, the flow rate calculating section 58 calculates the flow rate through step calculating. Therefore, the flow rate calculating section 58 has a function for producing several flow rates for calculation before calculation of a final flow rate and calculates a flow rate in object conditions from a plurality of thus produced calculating flow rates.

More particularly, the flow rate calculating section 58 uses those of the motor current flow rate-related data which relate to two impeller rotational speeds proximate to the impeller rotational speed value in data of two predetermined viscosity-related flow rate data storage functions proximate to the inputted viscosity value or the fluid viscosity value calculated from inputted fluid measurement data (particularly, a hematocrit value) (in other words, those two predetermined viscosity-related flow rate data tables whose fluid viscosities are proximate to the fluid viscosity value), and has a first calculating flow rate production function for using two those, which are proximate to the measured motor current, of the motor current flow rate-related data relating to one of the impeller rotational speed in one of the predetermined viscosity-related flow rate data to calculate the flow rate at the measured motor current through proportional calculation or in accordance with a regression expression calculated from the two motor current flow rate-related data or adopt, where the motor current flow rate-related data include stored flow rate data regarding a motor current equal to the measured motor current, the flow rate data.

Further, the flow rate calculating section 58 has a second calculating flow rate production function for using two those, which are proximate to the measured motor current, of the motor current flow rate-related data relating to the other impeller rotational speed in the one predetermined viscosity-related flow rate data to calculate the flow rate at the measured motor current through proportional calculation or in accordance with a regression expression calculated from the two motor current flow rate-related data or adopt, where the motor current flow rate-related data include stored flow rate data regarding a motor current equal to the measured motor current, the flow rate data.

The second calculating flow rate production function is different from the first calculating flow rate production function only in that, while the first calculating flow rate production function uses motor current flow rate-related data regarding one of the impeller rotational speed proximate to the impeller rotational speed value in one of the predetermined viscosity-related flow rate data, the second calculating flow rate production function uses motor current flow rate-related data regarding the other impeller rotational speed proximate to the impeller rotational speed value in the one predetermined viscosity-related flow rate data.

Further, the flow rate calculating section 58 has a third calculating flow rate production function for using two those, which are proximate to the measured motor current, of the motor current flow rate-related data relating to the one impeller rotational speed in the other predetermined viscosity-related flow rate data to calculate the flow rate at the measured motor current through proportional calculation or in accordance with a regression expression calculated from the two motor current flow rate-related data or adopt, where the motor current flow rate-related data include stored flow rate data regarding a motor current value to the measured motor current, the flow rate data.

The third calculating flow rate production function is different from the first calculating flow rate production function only in that, while the first calculating flow rate production function uses motor current flow rate-related data regarding one of the impeller rotational speed proximate to the impeller rotational speed value in one of the predetermined viscosity-related flow rate data, the third calculating flow rate production function uses motor current flow rate-related data regarding the one impeller rotational speed proximate to the impeller rotational speed value in the other predetermined viscosity-related flow rate data.

Further, the flow rate calculating section 58 has a fourth calculating flow rate production function for using two those, which are proximate to the measured motor current, of the motor current flow rate-related data relating to said other impeller rotational speed in said other predetermined viscosity-related flow rate data to calculate the flow rate at the measured motor current through proportional calculation or in accordance with a regression expression calculated from the two motor current flow rate-related data or adopt, where the motor current flow rate-related data include stored flow rate data regarding a motor current equal to the measured motor current, the flow rate data.

The fourth calculating flow rate production function is different from the first calculating flow rate production function described hereinabove only in that, while the first calculating flow rate production function uses motor current flow rate-related data regarding one of the impeller rotational speed proximate to the impeller rotational speed value in one of the predetermined viscosity-related flow rate data, the fourth calculating flow rate production function uses motor current flow rate-related data regarding said other impeller rotational speed proximate to the impeller rotational speed value in said other predetermined viscosity-related flow rate data.

The first to fourth calculating flow rate production functions use data of two predetermined viscosity-related flow rate data storage functions proximate to the inputted viscosity value or the fluid viscosity value calculated from inputted fluid measurement data (particularly a hematocrit value) (in other words, two predetermined viscosity-related data tables whose fluid viscosities are proximate to the fluid viscosity value). In particular, production of each calculating flow rate is performed using data of two ones of the predetermined viscosity-related data tables including a predetermined viscosity-related data table for a fluid viscosity lower than and most proximate to the fluid viscosity value and another predetermined viscosity-related data table for another fluid viscosity higher than and most proximate to the fluid viscosity value. It is to be noted that, where the fluid viscosity value is lower than the lowest one or higher than the highest one of the predetermined viscosity of the stored predetermined viscosity-related data tables, production of each calculating flow rate is performed using the data of two proximate ones of the predetermined viscosity-related data tables.

Similarly, production of each calculating flow rate is performed using motor current flow rate-related data regarding two impeller rotational speeds in the predetermined viscosity-related flow rate data tables which are proximate to the impeller rotational speed value. In short, production of each calculating flow rate is performed using data of two impeller rotational speeds including data regarding the impeller rotational speed lower than and most proximate to the impeller rotational speed value and data regarding the impeller rotational speed higher than and most proximate to the impeller rotational speed value. It is to be noted that, where the impeller rotational speed value is lower than the lowest one or higher than the highest one of the impeller rotational speeds of the stored predetermined impeller rotational speed data, production of each calculating flow rate is performed using the data of two proximate ones of the impeller rotational speed values.

Further, where motor current flow rate-related data most proximate to and lower than the measured motor current and motor current flow rate-related data most proximate to and higher than the measured motor current are present, production of each calculating flow rate is performed using the two motor current flow rate-related data through proportional calculation or in accordance with a regression expression calculated from the two motor current flow rate-related data. However, where motor current flow rate-related data most proximate to and lower than the measured motor current or motor current flow rate-related data most proximate to and higher than the measured motor current is not present, production of each calculating flow rate is performed using the two motor current flow rate-related data proximate to the measured motor current through proportional calculation or in accordance with a regression expression calculated from the two motor current flow rate-related data. On the other hand, where the motor current flow rate-related data include stored flow rate data regarding a motor current equal to the measured motor current, the flow rate data is adopted as the first calculating flow rate. In this instance, no calculation is performed, but merely selective adoption is performed.

Then, the flow rate calculating section 58 calculates the flow rate at the fluid viscosity value, the impeller rotational speed value and the measured motor current using the first to fourth calculating flow rates calculated by the first to fourth calculating flow rate production functions. It is to be noted that the calculating flow rate produced directly from the stored data described above can be represented as primary calculating flow rate. Then, the centrifugal fluid pump assembly of the present embodiment calculates two secondary calculating flow rates using the primary calculating flow rates and calculates a final flow rate using the two secondary calculating flow rates.

More particularly, the flow rate calculating section 58 includes a fifth calculating flow rate production function for using the first calculating flow rate regarding the one predetermined viscosities and the third calculating flow rate regarding the other predetermined viscosity to calculate a flow rate at the one impeller rotational speed at the fluid viscosity value through proportional calculation or in accordance with a regression expression calculated from the two calculating flow rate values.

The flow rate calculating section 58 further includes a sixth calculating flow rate production function for using the second calculating flow rate regarding the one predetermined viscosity and the fourth calculating flow rate regarding said other predetermined viscosity to calculate a flow rate at said other impeller rotational speed at the fluid viscosity value through proportional calculation or in accordance with a regression expression calculated from the two calculating flow rate values.

Further, the flow rate calculating section 58 includes a function for using the fifth and sixth calculating flow rates produced by the fifth calculating flow rate production function regarding the one impeller rotational speed and the sixth calculating flow rate production function regarding said other impeller rotational speed to calculate the flow rate at the impeller rotational speed through proportional calculation or in accordance with a regression expression calculated from the two calculating flow rates.

More detailed description is given below.

Motor current where the specific gravity of the fluid is 1 at flow rates 1, 2, 3, 4, 5, 6, 7, 8, 9 [L/min]

for each of rotational speeds 1200, 1400, 1600, 1800, 2000, 2200, 2400, 2600 [rpm]

at each of viscosities 1, 2, 3, 4, 5 [mPa·s]

are determined through an experiment in advance. It is to be noted that, for correction where the specific gravity is not 1, the motor current value then is divided by the specific gravity to obtain a normalized value.

Here, it is assumed that $V_m$=m [mPa·s] (m =1, 2, 3, 4, 5)

$N_m$=1000+200 m [rpm] (m =1, 2, 3, 4, 5, 6, 7, 8)

where m is a positive integer. In the following description, the viscosity is represented by v, the rotational speed by n, the flow rate by q, and the motor current by i.

Now, it is assumed that a viscosity value v0, a rotational speed n0 and a motor current i0 are given and it is intended to determine the flow rate then (since the viscosity and the specific gravity do not vary significantly with the same person although they differ depending upon individual differences of patients, if they are measured by periodical inspections, then a sufficient accuracy is obtained).

First, four adjacent data points (points at which the relationship between the flow rate and the motor current is determined through a measurement in advance) to this point (v0, n0) are determined.

In particular, m is varied to determine j which satisfies $$V_j < v_0 < V_{j+1}$$

Also with regard to the rotational speed, k which satisfies $$N_k < n0 < N_{k+1}$$

is determined. Consequently, the four adjacent data points are given by $$(V_j, N_k), (V_{j+1}, N_k), (V_j, N_{k+1}), (V_{j+1}, N_{k+1})$$

A relationship between the flow rate and the motor current in the four conditions given above is determined. In particular, since data points:

$(Q_m, I_m)$ m=1, 2, . . . , 9 are present, m which satisfies $$I_m < i0 < I_{m+1}$$

is determined. Then, using linear approximation for the interval $[Q_m, Q_{m+1}]$ (data points are measured at intervals with which a necessary accuracy is obtained through linear approximation in advance), the relational expression of (q, i) is $$i - I_m = [(I_{m+1} - I_m)/(Q_{m+1} - Q_m)](q - Q_m)$$

and therefore, q00: flow rate (calculated value) at $(V_j, N_k, i0)$ q10: flow rate (calculated value) at $(V_{j+1}, N_k, i0)$ q01: flow rate (calculated value) at $(V_j, N_{k+1}, i0)$ q11: flow rate (calculated value) at $(V_{j+1}, N_{k+1}, i0)$ can be determined.

From $(V_j, q00)$ and $(V_{j+1}, q10)$ where $N_k$ and i0 are equal, using linear approximation in the interval $[V_j, V_{j+1}]$, the relational expression of (v, q) is given by $$q - q00 = [(q10 - q00)/(V_{j+1} - V_j)](v - V_j)$$

and therefore, if the flow rate at v0 is represented by q20, then it is given by $$q20 = \{(q10 - q00)/(V_{j+1} - V_j)\}(v0 - V_j) + q00$$

Similarly, from $(V_j, q01)$ and $(V_{j+1}, q11)$ where $N_{k+1}$ and i0 are equal, if the flow rate at v0 is represented by q21, then it is given by $$q21 = [(q11 - q01)/(V_{j+1} - V_j)](v0 - V_j) + q01$$

In particular,
q20: flow rate (calculated value) at (v0, $N_k$, i0)
q21: flow rate (calculated value) at (v0, $N_{k+1}$, i0)
are determined.

Then, using linear approximation in the interval [$N_k$, $N_{k+1}$], the relational expression of (n, q) is given by $$q - q20 = [(q21 - q20)/(N_{k+1} - N_k)](n - N_k)$$

and therefore, the flow rate q0 at (v0, n0, i0) to be determined finally is given by $$q0 = [(q21 - q20)/(N_{k+1} - N_k)](n0 - N_k) + q20$$

As a particular example, a process of determination of the flow rate in the conditions of a viscosity value of 3.8 [mPa·s], a rotational speed of 1950 [rpm] and a motor current of 0.28 [A] (value obtained by dividing the actually measured current of 0.3 A by the specific gravity of 1.07) is illustrated in FIG. 7. The calculation process is such as given below.

(1) Selection of calculating utilization data

The following four data points are adjacent data points to 3.8 mPa·s, 1950 rpm.

The flow rate is calculated from the characteristic of the "current and flow rate" at totaling eight points including:

(0.27 A, 5 L/min: x1, y1), (0.31 A, 6 L/min: x2, y2) at 1800 rpm of the data table for the viscosity of 3 mPa·s of FIG. 10, (0.27 A, 3 L/min: x3, y3), (0.30 A, 4 L/min: x4, y4) at 2000 rpm, (0.27 A, 4 L/min: x5, y5), (0.30 A, 5 L/min: x6, y6) at 1800 rpm of the data table for the viscosity of 4 mPa·s of FIG. 11, and (0.26 A, 2 L/min: x7, y7), (0.29 A, 3 L/min: x8, y8) at 2000 rpm.

It is to be noted that, if data of a value equal to the motor current value of the object of the calculation is stored in a data table, then the value is used. Therefore, data at four points in the minimum are used, and data at eight points in the maximum described above are used.

(2) Production of first to fourth calculating flow rates (production of primary calculating flow rates)

If the flow rate at the viscosity of 3 mPa·s, the rotational speed of 1800 rpm and the motor current of 0.28 A is calculated from (0.27 A, 5 L/min: x1, y1), (0.31 A, 6 L/min: x2, y2) at 1800 rpm of the data table for the viscosity of 3 mPa·s of FIG. 10, then ((0.28 A), 3 mPa·s, 5.25 L/min: xa, ya) is obtained. Thus, the first calculating flow rate is calculated.

Similarly, if the flow rate at the viscosity of 3 mPa·s, the rotational speed of 2000 rpm and the motor current of 0.28 A is calculated from (0.27 A, 3 L/min: x3, y3), (0.30 A, 4 L/min: x4, y4) at 2000 rpm, then ((0.28 A), 3 mPa·s, 3.33 L/min: xb, yb) is obtained. Thus, the second calculating flow rate is calculated.

If the flow rate at the viscosity of 4 mPa·s, the rotational speed of 1800 rpm and the motor current of 0.28 A is calculated from (0.27 A, 4 L/min: x5, y5), (0.30 A, 5 L/min: x6, y6) at 1800 rpm of the data table for the viscosity of 4 mPa·s of FIG. 11, then ((0.28 A), 4 mPa·s, 4.33 L/min: xc, yc) is obtained. Thus, the third calculating flow rate is calculated.

Similarly, if the flow rate at the viscosity of 4 mPa·s, the rotational speed of 2000 rpm and the motor current of 0.28 A is calculated from (0.26 A, 2 L/min: x7, y7), (0.29 A, 3 L/min: x8, y8) at 2000 rpm, then ((0.28 A), 4 mPa·s, 2.66 L/min: xd, yd) is obtained. Thus, the fourth calculating flow rate is calculated.

It is to be noted that, where data of a value equal to the motor current value of the object of the calculation is stored in the data tables, the value is produced as a pertaining one of the first to fourth calculating flow rates.

(3) Production of fifth and sixth calculating flow rates (production of secondary calculating flow rates)

Then, since what is to be determined is the flow rate at 3.8 mPa·s, if the first calculating flow rate (3 mPa·s, 5.25 L/min: xa, ya) and the third calculating flow rate (4 mPa·s, 4.33 L/min: xc, yc) are used to calculate the flow rate at the viscosity value of 3.8 mPa·s, the rotational speed of 1800 rpm and the motor current of 0.28 A, then ((3.8 mPa·s, 0.28 A), 1800 rpm, 4.51 L/min: xe, ye). Thus, the fifth calculating flow rate is calculated.

Similarly, since what is to be determined is the flow rate at 3.8 mPa·s, if the second calculating flow rate (3 mPa·s, 3.33 L/min : xb, yb) and the fourth calculating flow rate (4 mPa·s, 2.66 L/min: xd, yd) are used to calculate the flow rate at the viscosity value of 3.8 mPa·s, the rotational speed of 2000 rpm and the motor current of 0.28 A, then ((3.8 mPa·s, 0.28 A), 2000 rpm, 2.79 L/min : xf, yf). Thus, the sixth calculating flow rate is calculated.

(4) Calculation of flow rate

Finally, since what is to be determined is the flow rate at 1950 rpm, if the fifth calculating flow rate (1800 rpm, 4.51 L/min: xe, ye) and the sixth calculating flow rate (2000 rpm, 2.79 L/min: xf, yf) are used to calculate the flow rate at the rotational speed of 1950 rpm, the motor current of 0.28 A and the viscosity of 3.8 mPa·s, then ((3.8 mPa·s, 0.28 A), 1950 rpm, 3.22 L/min: xe, ye). Thus, the flow rate is calculated.

The calculation of the fifth and sixth calculating flow rates (secondary calculating flow rates) and the calculation of the flow rate described above by the flow rate calculating section may otherwise be such as described below.

The flow rate calculating section 58 in this instance has a fifth calculating flow rate production function for using the first calculating flow rate value relating to one of the predetermined viscosity and the second calculating flow rate relating to the one predetermined viscosity to calculate the flow rate at the impeller rotational speed value at the one predetermined viscosity through proportional calculation or in accordance with a regression expression calculated from the two calculating flow rates.

The flow rate calculating section 58 further has a sixth calculating flow rate production function for using the third calculating flow rate relating to the other predetermined viscosity and the fourth calculating flow rate relating to the other predetermined viscosity to calculate the flow rate at the impeller rotational speed value at the other predetermined viscosity through proportional calculation or in accordance with a regression expression calculated from the two calculating flow rates.

Further, the flow rate calculating section 58 has a function for using the fifth and sixth calculating flow rates produced by the fifth calculating flow rate production function regarding the one predetermined viscosity and the sixth calculating flow rate production function regarding the other predetermined viscosity to calculate the flow rate at the fluid viscosity value through proportional calculation or in accordance with a regression expression calculated from the two calculating flow rates.

In short, the calculation of the flow rate is not limited to the calculating method described above, but the flow rate may otherwise be calculated by calculating the flow rate at the viscosity of 3 mPa·s, the rotational speed of 1950 rpm and the motor current of 0.28 A using the first calculating flow rate and the second calculating flow rate to calculate the fifth calculating flow rate, calculating the flow rate at the viscosity of 4 mPa·s, the rotational speed of 1950 rpm and the motor current of 0.28 A using the third calculating flow rate and the fourth calculating flow rate to calculate the sixth calculating flow rate and then finally calculating the flow rate at the viscosity of 3.8 mPa·s as indicated by broken lines in FIG. 7. Detailed description is given below. It is to be noted that also the present calculating method of the flow rate similarly includes (1) selection of calculating utilization data and (2) production of first to fourth calculating flow rates (production of primary calculating flow rates) described above.

(3') Production of fifth and sixth calculating flow rates (production of secondary calculating flow rates)

Since what is to be determined is the flow rate at 1950 rpm, if the first calculating flow rate (1800 rpm, 5.25 L/min : xa, ya) and the second calculating flow rate (2000 rpm, 3.33 L/min: xb, yb) are used to calculate the flow rate at the viscosity value of 3 mPa·s, the rotational speed of 1950 rpm and the motor current of 0.28 A, then ((1950 rpm, 0.28 A), 3 mPa·s, 3.81 L/min: xe, ye) is obtained. Thus, the fifth calculating flow rate is calculated. Similarly, since what is to be determined is the flow rate at 1950 rpm, if the third calculating flow rate (1800 rpm, 4.33 L/min: xc, yc) and the fourth calculating flow rate (2000 rpm, 2.66 L/min: xd, yd) are used to calculate the flow rate at the viscosity value of 4 mPa·s, the rotational speed of 1950 rpm and the motor current of 0.28 A, then ((1950 rpm, 0.28 A), 4 mPa·s, 3.08 L/min: xf, yf) is obtained. Thus, the sixth calculating flow rate is calculated.

(4') Calculation of flow rate

Finally, since what is to be determined is the flow rate at 3.8 mPa·s, if the fifth calculating flow rate (3 mPa·s, 3.81 L/min : xe, ye) and the sixth calculating flow rate (4 mPa·s, 3.077 L/min: xf, yf) are used to calculate the flow rate at the rotational speed of 1950 rpm, the motor current of 0.28 A and the viscosity of 3.8 mPa·s, then ((1950 rpm, 0.28 A), 3.8 mPa·s, 3.22 L/min: xe, ye) is obtained. Thus, the flow rate is calculated.

With the centrifugal fluid pump assembly of the particular embodiment described above, since the flow rate can be calculated through repetitions of a simple subroutine including the proportional calculation or the linear approximation (in other words, linear regression expression), the data capacity and the storage capacity for expressions for calculation and so forth can be reduced and also the calculating processing is facilitated. Consequently, the centrifugal fluid pump assembly can be incorporated even into a portable controller and also facilitates display on the real time basis.

The flow rate calculated by the flow rate calculating section is displayed on the display section 59.

Figure 13:
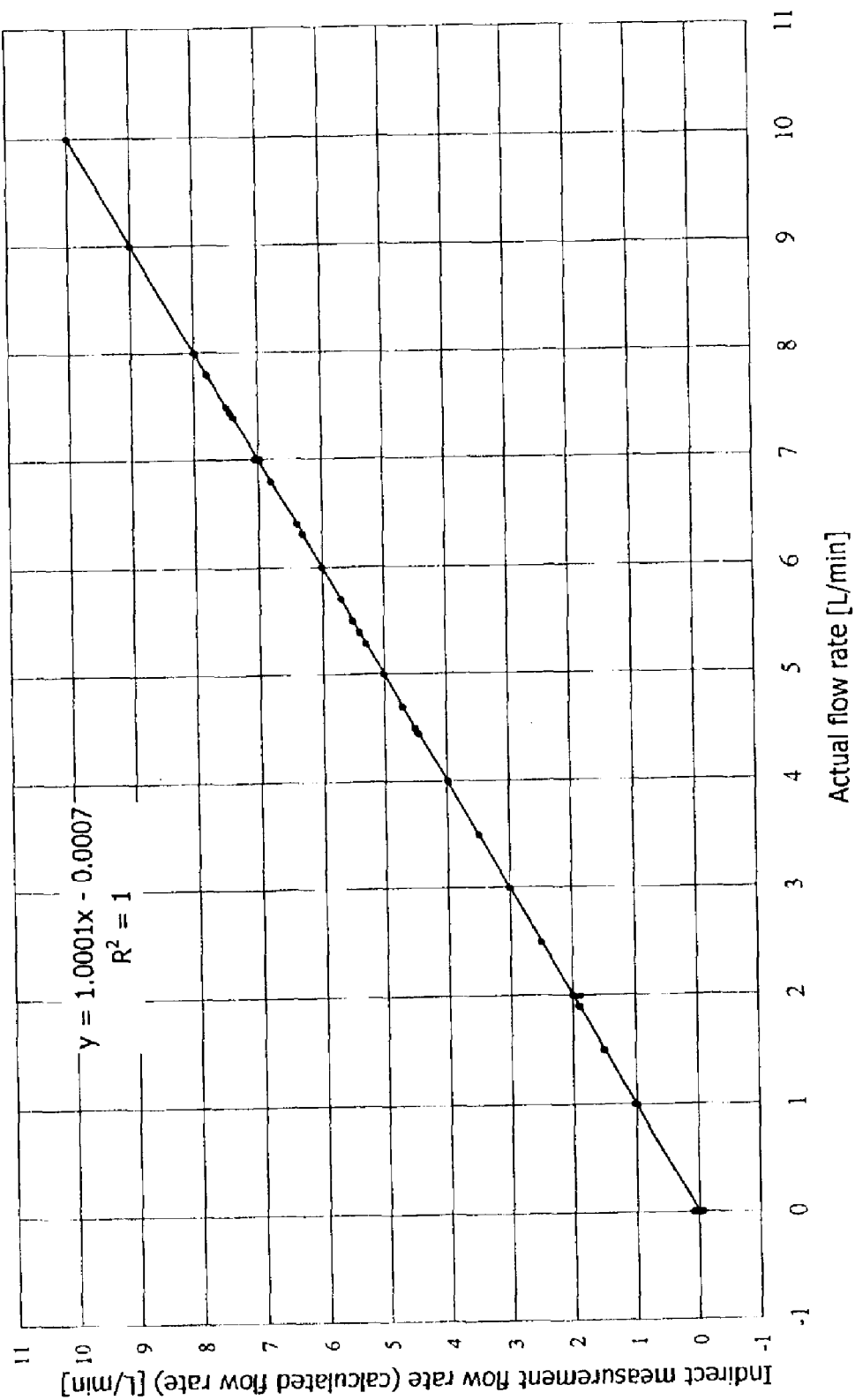
FIG. 13 is a graph illustrating a result of calculation of the flow rate in the centrifugal fluid pump assembly of the embodiment of the present invention.

An example of the relationship between the indirect measurement flow rate obtained using the method described above and the actual flow rate is illustrated in FIG. 13. In FIG. 13, although a plurality of indirect measurement flow rates are indicated for each actual flow rate, they coincide almost with the latter. Originally, according to the present method, the accuracy in the proximity of a measurement point is high, and therefore, the error between them at the measurement point is very small. However, since the present method is essentially linear approximation, it can be recognized readily that an estimated value between any two measurement points falls on the straight line and a high correlation is exhibited.

Figure 14:
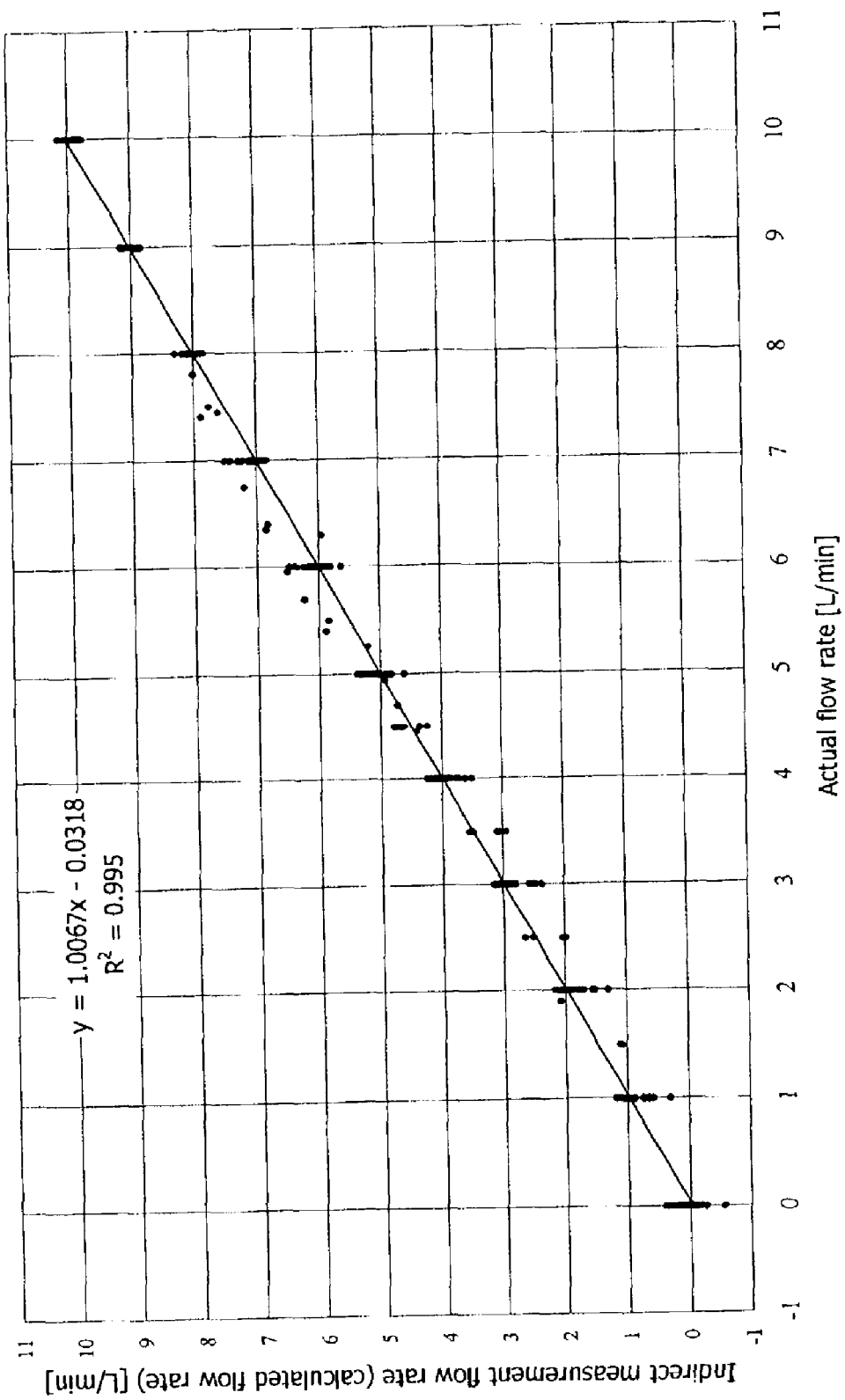
FIG. 14 is a graph illustrating a result of calculation of the flow rate in a centrifugal fluid pump assembly of a comparative example.

In contrast, a relationship between the indirect measurement flow rate where the relational expression (1) given hereinabove is used for the same data and the actual flow rate is shown in FIG. 14. Also in FIG. 14, a plurality of indirect measurement flow rates are found for each actual flow rate, but they do not coincide very much with the latter. In particular, the difference between them directly represents the error.

It is to be noted that, also where the point (v0, n0) is outside the data points like, for example, $V_s < v0,$ $N_8 < n0$ the indirect measurement flow rate can be determined similarly by extending (extrapolation) the straight line individually in the nearest intervals:

$[V_4, V_5]$ $[N_7, N_8]$

Also with regard to the relationship between the flow rate and the motor current, where given conditions are outside the data points, the countermeasure through extrapolation described above can be applied similarly.

Figure 6:
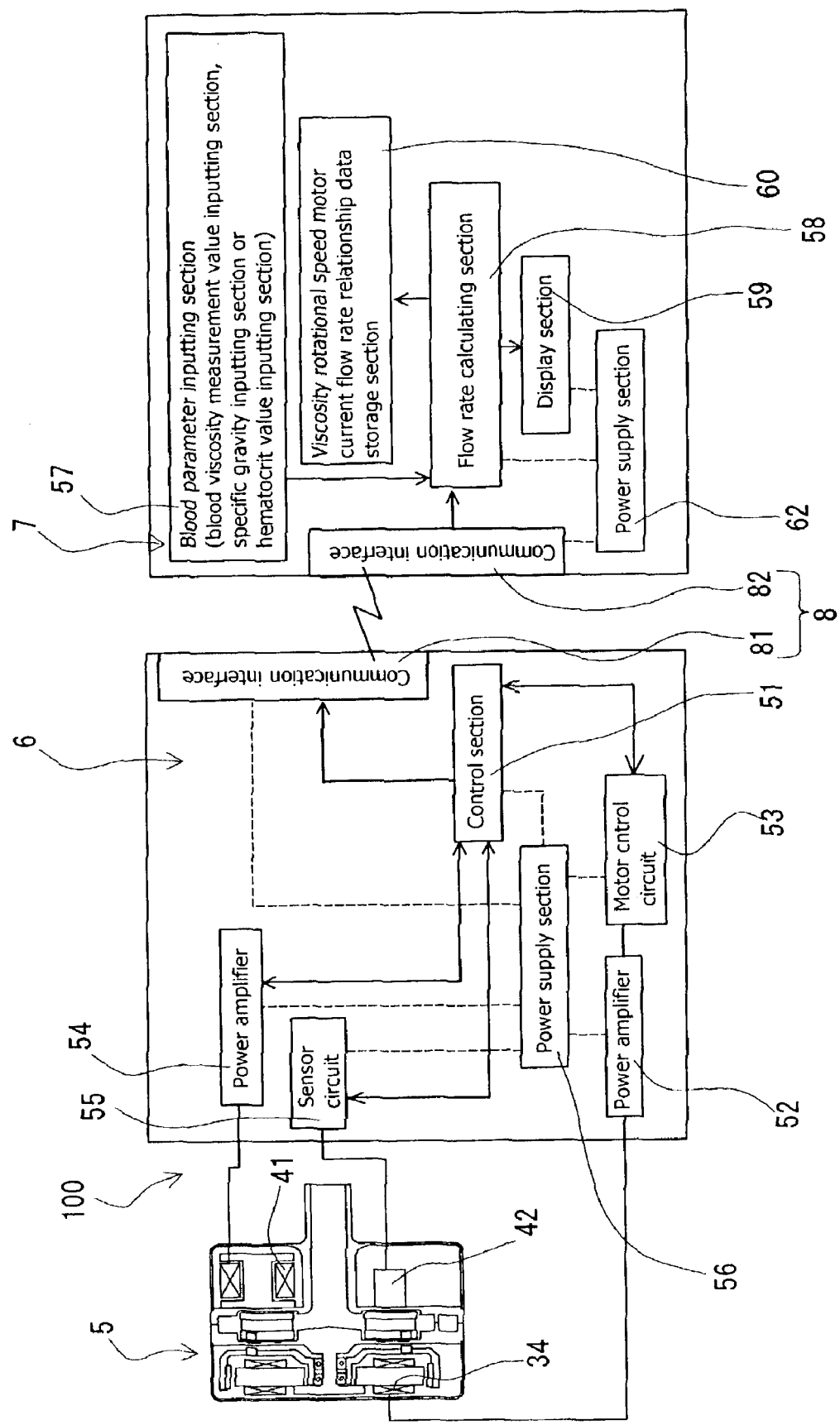
FIG. 6 is a block diagram of another embodiment of the centrifugal pump assembly of the present invention.

The centrifugal pump assembly may otherwise be of such a type as shown in FIG. 6. Referring to FIG. 6, the centrifugal pump assembly 100 of the present embodiment includes a centrifugal fluid pump assembly body including a centrifugal fluid pump assembly body section 5 and a control mechanism (in other words, controller) 6 electrically connected to the centrifugal fluid pump assembly body section 5, and a flow rate calculating section 7 separate from the centrifugal fluid pump assembly body. The control mechanism 6 and the flow rate calculating section 7 have a communication function 8 so that data can be communicated therebetween. In particular, the communication function 8 includes a control mechanism side communication interface 81 (controller side communication interface) and a flow rate calculator side communication interface 82. At least the control mechanism side communication interface 81 (controller side communication interface) has a function of originating a motor current or a signal relating to the motor current value, and the flow rate calculator communication interface 82 has a function of receiving the motor current value or the signal relating to the motor current value originated from the control mechanism side communication interface 81. It is to be noted that the communication between them may be any analog communication and digital communication. A known communication interface can be used as the communication form. The centrifugal fluid pump assembly 100 of the present embodiment is different from the centrifugal fluid pump assembly 1 described hereinabove only in that the flow rate calculator is separate from the control mechanism, but is common in the configuration of the other part to that of the centrifugal fluid pump assembly 1 described above.

The control mechanism 6 in the centrifugal fluid pump assembly 100 of the present embodiment includes, as shown in FIG. 6, a power amplifier 52 and a motor control circuit 53 for the motor 34 for magnetic coupling, a power amplifier 54 for the electromagnets 41, a sensor circuit or sensor output monitoring section 55 for monitoring outputs of the sensor 42, a control section 51, a power supply section 56, and a control mechanism side communication interface 81. The control section 51 has a motor current monitoring function.

The flow rate calculating section 7 includes a fluid measurement data inputting section (in other words, blood parameter inputting section) 57, a flow rate calculating section 58, a display section 59, a motor current flow rate-related data storage section (in other words, viscosity rotational speed motor current flow rate-related data storage section) 60, a power supply section 62, and a flow rate calculator side communication interface 82.

The fluid measurement data inputting section (blood parameter inputting section) 57 is, for example, a fluid viscosity measurement value inputting section. Preferably, the fluid measurement data inputting section 57 includes a blood viscosity measurement value inputting section and a specific gravity inputting section as shown in FIG. 6. In this instance, the blood viscosity and the specific gravity are measured with blood gathered from a user using an external instrument.

The fluid measurement data inputting section (blood parameter inputting section) 57 may be a hematocrit value inputting section as indicated in FIG. 6. In this instance, the centrifugal fluid pump assembly has a viscosity calculating function for calculating the viscosity from the inputted hematocrit value. In short, the flow rate calculating section 58 has a viscosity calculating function.

The configuration of the other part is same as that of the embodiment described hereinabove.

A centrifugal fluid pump assembly of the present invention which includes a housing having a fluid inlet and a fluid outlet, an impeller rotatable within the housing for feeding fluid by centrifugal force upon rotation thereof, and a motor for rotating the impeller, comprises a motor current flow rate-related data storage section for storing, for a plurality of different predetermined viscosities, predetermined viscosity-related flow rate data formed from a plurality of motor current flow rate relation data at a plurality of different impeller rotational speeds at predetermined fluid viscosity, a fluid measurement data inputting section, an impeller rotational speed measurement function or an impeller rotational speed calculation function, a motor current measurement function, and a flow rate calculating section for calculating, using a fluid viscosity value inputted to the fluid measurement data inputting section or calculated from fluid measurement data inputted to the fluid measurement data inputting section, an impeller rotational speed value obtained by the impeller rotational speed measurement function or impeller rotational speed calculation function, a measured motor current obtained by the motor current measurement function and the data stored in the motor current flow rate-related data storage section, a fluid flow rate at the fluid viscosity value, measured motor current and impeller rotational speed value.

With the present centrifugal fluid pump assembly, the fluid flow rate (discharge) can be calculated readily and with certainty without using a flow meter. Further, since minimum discrete data with which a necessary accuracy can: be satisfied are stored without having a relational expression of the speed of rotation, motor current, viscosity and flow rate and those stored data which are proximate to an motor current value and so forth of an object of calculation are used to calculate the flow rate, it is possible for the centrifugal fluid pump to get more accurate flow rate than flow rate calculated with polynomial regression expression.

While the preferred form of the present invention has been described, it is to be understood that modifications will be apparent to those skilled in the art without departing from the spirit of the invention. The scope of the invention, therefore, is to be determined solely by the following claims.

What is claimed is:

1. A centrifugal fluid pump assembly which includes a housing having a fluid inlet and a fluid outlet, an impeller rotatable within said housing for feeding fluid by centrifugal force upon rotation thereof, and a motor for rotating said impeller, comprising:

a motor current flow rate-related data storage section for storing, for a plurality of different predetermined viscosities, predetermined viscosity-related flow rate data formed from a plurality of motor current flow rate relation data at a plurality of different impeller rotational speeds at predetermined fluid viscosity;

a fluid measurement data inputting section;

an impeller rotational speed measurement function or an impeller rotational speed calculation function;

a motor current measurement function;

a flow rate calculating section for calculating a fluid flow rate using 1) a fluid viscosity value inputted to said fluid measurement data inputting section or calculated from a fluid measurement data inputted to said fluid measurement data inputting section, 2) an impeller rotational speed value obtained by said impeller rotational speed measurement function or impeller rotational speed calculation function, 3) a measured motor current obtained by said motor current measurement function and 4) the data stored in said motor current flow rate-related data storage section;

wherein said motor current flow rate-related data storage section comprises at least a first predetermined viscosity-related flow rate data storage function for storing a plurality of data regarding the motor current and the flow rate at a plurality of impeller rotational speeds at a first predetermined fluid viscosity, a second predetermined viscosity-related flow rate data storage function for storing a plurality of data regarding the motor current and the flow rate at a plurality of impeller rotational speeds at a second predetermined fluid viscosity, and a third predetermined viscosity-related flow rate data storage function for storing a plurality of data regarding the motor current and the flow rate at a plurality of impeller rotational speeds at a third predetermined fluid viscosity;

a specific gravity inputting section or specific gravity calculating function; and a measured motor current correcting function for correcting the measured motor current using a specific gravity inputted by said specific gravity inputting section or calculated by said specific value calculating function.

2. A centrifugal fluid pump assembly according to claim 1, comprising a centrifugal fluid pump section including said housing having said fluid inlet and said fluid outlet and said impeller having magnetic means and rotatable within said housing, an impeller rotating torque generation section including a rotor having magnetic means for attracting said magnetic means of said impeller and said motor for rotating said rotor, and an impeller position control section including electromagnet means, and wherein said impeller rotates in a non-contacting relationship with said housing.

3. A centrifugal fluid pump assembly according to claim 1, wherein said fluid measurement data inputting section is a fluid viscosity measurement value inputting section, and the fluid viscosity value is a fluid viscosity measurement value.

4. A centrifugal fluid pump assembly according to claim 1, wherein said fluid measurement data inputting section is a hematocrit value inputting section, and said centrifugal fluid pump assembly further comprises a viscosity calculating function for calculating the viscosity from the inputted hematocrit value.

5. A centrifugal fluid pump assembly according to claim 1, wherein said fluid measurement data inputting section is a hematocrit value inputting section, and said centrifugal fluid pump assembly further comprises a viscosity calculating section for calculating the viscosity from the inputted hematocrit value and a specific gravity calculating section for calculating a specific gravity from the inputted hematocrit value.

6. A centrifugal fluid pump assembly according to claim 1, wherein said motor current flow rate-related data storage section further includes a fourth predetermined viscosity-related flow rate data storage function for storing a plurality of data regarding the motor current and the flow rate at a plurality of impeller rotational speeds at a fourth predetermined fluid viscosity.

7. A centrifugal fluid pump assembly according to claim 6, wherein said motor current flow rate-related data storage section further includes a fifth predetermined viscosity-related flow rate data storage function for storing a plurality of data regarding the motor current and the flow rate at a plurality of impeller rotational speeds at a fifth predetermined fluid viscosity.

8. A centrifugal fluid pump assembly according to claim 1, wherein the data stored in the predetermined viscosity-related flow rate data storage functions include a plurality of stored data regarding the motor current and the flow rate at a plurality of equal impeller rotational speeds.

9. A centrifugal fluid pump assembly according to claim 1, wherein said flow rate calculating section calculates the fluid flow rate using data of two of the predetermined viscosity-related flow rate data storage functions whose fluid viscosities are proximate to the fluid viscosity value.

10. A centrifugal fluid pump assembly according to claim 1, wherein, if the fluid viscosity value is equal to the predetermined viscosity of any of the predetermined viscosity-related flow rate data storage functions, said flow rate calculating section uses the data of the predetermined viscosity-related flow rate data storage function to calculate the flow rate.

11. A centrifugal fluid pump assembly according to claim 1, wherein said flow rate calculating section calculates the flow rate using the motor current flow rate relation data relating to two impeller rotational speeds proximate to the impeller rotational speed value in the data of two of the predetermined viscosity-related flow rate data storage functions whose fluid viscosities are proximate to the fluid viscosity value.

12. A centrifugal fluid pump assembly according to claim 1, wherein said flow rate calculating section calculates the flow rate using the motor current flow rate relation data which relate to two impeller rotational speeds proximate to the impeller rotational speed value in the data of two of the predetermined viscosity-related flow rate data storage functions proximate to the fluid viscosity value, the flow rate calculating section comprising a first calculating flow rate production function for using two of the motor current flow rate-related data relating to one of the impeller rotational speed in one of the predetermined viscosity-related flow rate data and proximate to the measured motor current to calculate the flow rate at the measured motor current through proportional calculation or in accordance with a regression expression calculated from the two motor current flow rate-related data or by adopting, where the motor current flow rate-related data include stored flow rate data regarding a motor current equal to the measured motor current, the flow rate data, a second calculating flow rate production function for using two of the motor current flow rate-related data relating to the other impeller rotational speed in the one predetermined viscosity-related flow rate data and proximate to the measured motor current to calculate the flow rate at the measured motor current through proportional calculation or in accordance with a regression expression calculated from the two motor current flow rate-related data or by adopting, where the motor current flow rate-related data include stored flow rate data regarding a motor current equal to the measured motor current, the flow rate data, a third calculating flow rate production function for using two of the motor current flow rate-related data relating to the one impeller rotational speed in the other predetermined viscosity-related flow rate data and proximate to the measured motor current to calculate the flow rate at the measured motor current through proportional calculation or in accordance with a regression expression calculated from the two motor current flow rate-related data or by adopting, where the motor current flow rate-related data include stored flow rate data regarding a motor current equal to the measured motor current, the flow rate data, and a fourth calculating flow rate production function for using two of the motor current flow rate-related data relating to said other impeller rotational speed in said other predetermined viscosity-related flow rate data and proximate to the measured motor current to calculate the flow rate at the measured motor current through proportional calculation or in accordance with a regression expression calculated from the two motor current flow rate-related data or by adopting, where the motor current flow rate-related data include stored flow rate data regarding a motor current equal to the measured motor current, the flow rate data, and said flow rate calculating section calculates the flow rate using the first to fourth calculating flow rates calculated by the first to fourth calculating flow rate production functions.

13. A centrifugal fluid pump assembly according to claim 12, wherein said flow rate calculating section further includes a fifth calculating flow rate production function for using the first calculating flow rate regarding the one predetermined viscosity and the third calculating flow rate regarding the other predetermined viscosity to calculate a flow rate at the one impeller rotational speed and at the fluid viscosity value, a sixth calculating flow rate production function for using the second calculating flow rate regarding the one predetermined viscosity and the fourth calculating flow rate regarding said other predetermined viscosity to calculate a flow rate at said other impeller rotational speed and at the fluid viscosity value, and a function for using the fifth calculating flow rate produced by said fifth calculating flow rate production function regarding the one impeller rotational speed and said sixth calculating flow rate produced by said sixth calculating flow rate production function regarding said other impeller rotational speed to calculate the flow rate at the impeller rotational speed value.

14. A centrifugal fluid pump assembly according to claim 12, wherein said flow rate calculating section includes a fifth calculating flow rate production function for using the first calculating flow rate relating to the one predetermined viscosity and the second calculating flow rate relating to the one predetermined viscosity to calculate the flow rate at the impeller rotational speed value and at the one predetermined viscosity, a sixth calculating flow rate production function for using the third calculating flow rate relating to said other predetermined viscosity and the fourth calculating flow rate relating to said other predetermined viscosity to calculate the flow rate at the impeller rotational speed value and at said other predetermined viscosity, and a function for using the fifth calculating flow rate produced by said fifth calculating flow rate production function regarding the one predetermined viscosity and said sixth calculating flow rate produced by said sixth calculating flow rate production function regarding said other predetermined viscosity to calculate the flow rate at the fluid viscosity value.

* * * * *

UNITED STATES PATENT AND TRADEMARK OFFICE
CERTIFICATE OF CORRECTION

PATENT NO. : 7,033,147 B2
APPLICATION NO. : 10/352098
DATED : April 25, 2006
INVENTOR(S) : Masamichi Yanai et al.

It is certified that error appears in the above-identified patent and that said Letters Patent is hereby corrected as shown below:

In column 1, line 53, after "drop" insert --in--.
In column 2, line 30, after "section" insert --.--;
    line 31, change "for calculation, using" to --The flow rate calculation section uses --;
    line 39, change "section," to --section. The flow rate calculation section calculates--.
In column 3, line28, change "viscosity," to --viscosity. The fluid pump assembly also includes--;
    line 34, after "58" insert --. The flow rate calculating section 58 uses--;
    line 42, change "60 to calculate" to --60. The flow rate calculating section 58 calculates--.
    line 63, change "thereof," to --thereof. The fluid pump assembly also includes--;
    line 67, change "31, and a" to --31. Further the fluid pump assembly includes an--;
In column 4, line 13, change "a" (fourth occurrence) to --the--;
    line 14, change "an" to --the;--
    line 16, change "an" to --the;--
    line 23, delete "with";
    line 24, delete "an";
    line 48, change "are communicated" to --communicates--;
    line 55, change "angle" to --angular intervals--.
In column 5, line 36, change "angle" to --angular intervals--;
    line 37, after "ment" insert --and--;
    line 54, change "angle" to --angular intervals--;
    line 56, change "angle" to --angular intervals--.
In column 7, line 7, delete "viscosity rotational speed";
    line 13, delete "viscosity rotational speed";
    lines 16-17, delete "viscosity rotational speed".
In column 8, line 17, delete "viscosity rotational speed".
In column 9, lines 2-3, change "value), and" to --value). The flow rate calculating section 58--;
    line 4, change "those," to --of the motor current flow rate-related data relating to one of the impeller rotational speed in one of the predetermined viscosity-related flow rate data, and--;
    line 5, after "current" (first occurrence) change "," to --.--; delete 'of the motor current flow rate-related data relating";
    line 6, delete in its entirety;
    line 7, delete "termined viscosity related flow rate data";
    line 8, after "current" insert --. The calculation can be made--;

UNITED STATES PATENT AND TRADEMARK OFFICE
CERTIFICATE OF CORRECTION

PATENT NO. : 7,033,147 B2
APPLICATION NO. : 10/352098
DATED : April 25, 2006
INVENTOR(S) : Masamichi Yanai et al.

It is certified that error appears in the above-identified patent and that said Letters Patent is hereby corrected as shown below:

In column 9 (continued),
    line 11, change "adopt" to --by adopting--;
    lines 16; delete in its entirety;
    line 19, after "data" insert --, and which are proximate to the measured motor current,--;
    line 20, after "current" insert --. The calculation can be made--;
    line 22, change "adopt" to --by adopting--;
    line 39, delete in its entirety;
    line 42, after "data" insert --, and which are proximate to the measured motor current,--;
    line 43, after "current" insert --. The calculation can be made--;
    line 45, change "adopt" to --by adopting--;
    line 47, after "value" insert --equal--;
    line 62, delete in its entirety;
    line 65, after "data" insert --, and which are proximate to the measured motor current,--;
    line 66, after "current" insert --. The calculation can be made--.
In column 10, line 1, change "adopt" to --by adopting--;
    line 25, delete "ones";
    line 52, after "data," insert --the--;
    line 58, after "present," insert --the--.
In column 11, line 25, change "viscosities" to --viscosity--.
In column 12, line 3, delete "then";
    line 15, change "$V_j<v_0<V_{j+1}$" to --$V_j<v0<V_{j+1}$--.
In column 15, line 11, change "Detailed" to --A detailed--.
In column 16, line 55, change "common" to --similar--;
    line 56, change "part to that" to --parts--.
In column 17, line 36, after "viscosity" change "," to --.--; before "a" insert --The assembly also comprises--;
    line 40, after "section" insert --.--; change "for" to --The flow rate--;
    line 41, change "using" to --section uses--;
    line 49, after "section" change "," to --.--; change "a fluid" to --The--; after "rate" insert --section calculates a fluid flow rate--;

UNITED STATES PATENT AND TRADEMARK OFFICE
CERTIFICATE OF CORRECTION

PATENT NO. : 7,033,147 B2
APPLICATION NO. : 10/352098
DATED : April 25, 2006
INVENTOR(S) : Masamichi Yanai et al.

It is certified that error appears in the above-identified patent and that said Letters Patent is hereby corrected as shown below:

In column 17 (continued),
line 58, change "an" to --a--.

Signed and Sealed this

Twenty-sixth Day of June, 2007

JON W. DUDAS
*Director of the United States Patent and Trademark Office*